United States Patent [19]
Hofmann et al.

[11] 3,992,519
[45] Nov. 16, 1976

[54] ORAL HYGIENE COMPOSITIONS

[75] Inventors: Eberhard Hofmann, Hochdahl-Willbeck; Heinz Albert Gritz, Benrath-Urdenbach; Otto Vlazak, Hochdahl-Millrath, all of Germany

[73] Assignee: Beecham Group Limited, England

[22] Filed: July 24, 1975

[21] Appl. No.: 598,853

[30] Foreign Application Priority Data
Aug. 1, 1974 United Kingdom............... 33951/74

[52] U.S. Cl................................ 424/48; 424/49; 424/52; 424/54; 424/55; 424/57
[51] Int. Cl.$^2$........................................ A61K 7/22
[58] Field of Search............................ 424/49–58, 424/48

[56] References Cited
UNITED STATES PATENTS

| | | | |
|---|---|---|---|
| 2,218,172 | 10/1940 | Kokatnur | 424/48 |
| 3,170,916 | 2/1965 | Dziengel | 424/58 |
| 3,574,823 | 4/1971 | Roberts et al. | 424/49 |

FOREIGN PATENTS OR APPLICATIONS

| | | | |
|---|---|---|---|
| 1,593,977 | 7/1970 | France | 424/57 |
| 7,110,437 | 3/1971 | Japan | 424/56 |

*Primary Examiner*—Lewis Gotts
*Assistant Examiner*—Cary Owens

[57] ABSTRACT

Oral hygiene composition in toothpaste, mouthwash or chewing gum form comprising 0.1 to 5.0% of antibacterial component, 0.1 to 5.0% of vitamin component and 0.1 to 5.0% of surfactant component, all by weight of total composition. The antibacterial component is, e.g. an ester of p- or o-hydroxybenzoic acid. The vitamin component is, e.g. aescin, rutin, panthenol, nicotinamide or vitamin E. The surfactant component is anionic, e.g. a fatty alkylsulphate or alkylethersulphate, or a cationic quaternary surfactant. Anticariogenic fluorides may also be present.

11 Claims, No Drawings

ORAL HYGIENE COMPOSITIONS

This invention relates to oral hygiene compositions which have a beneficial effect in the prophylaxis and treatment of inflammatory diseases of the periodontium.

The periodontium is the name given to the tissues in which teeth are supported and embedded. The most common diseases of the periodontium are those involving inflammation, namely gingivitis (usually thought of as simple inflammation of the gums) and periodontitis (which, in addition to an inflammtion of the gums, involves movement of the epithelium of the gingival crevice, leading to pocket formation, destruction of the collagen fibres of the periodontal ligaments and resorption of the alveolar bone).

In the past, benefits have been claimed in the prophylaxis and treatment of inflammatory diseases of the periodontium from the application within the oral cavity of compositions containing antibacterial agents and/or vitamins and vitamin-like materials. Despite the claims which have from time to time been made, the known compositions have apparently failed to meet the requirements of the dental profession and the consumer, because of problems such as lack of proven efficacy, associated undesirable side effects and unpleasant taste.

According to the present invention there is provided an oral hygiene composition comprising an antibacterial component in an amount of from 0.1 to 5.0%, a vitamin component in an amount of from 0.1 to 5.0% and a surfactant component in an amount of from 0.1 to 5.0%, these percentages being by weight of the total composition, the weight ratio of antibacterial component to surfactant being from 1:5 to 5:1, the antibacterial component comprising one or more pharmaceutically acceptable esters of p-hydroxybenzoic acid and/or one or more pharmaceutically acceptable esters of o-hydroxybenzoic acid, and the vitamin component comprising one or more of the following aescin, rutin, panthenol, nicotinamide and vitamin E, it being understood that no ingredient of the total composition is present in more than a pharmaceutically acceptable amount.

Preferably the antibacterial component comprises 10 to 40% by weight of one or more pharmaceutically acceptable esters of p-hydroxybenzoic acid and 30 to 90% by weight of one or more pharmaceutically acceptable esters of o-hydroxybenzoic acid.

Examples of pharmaceutically acceptable esters of p- and o-hydroxybenzoic acid are the $C_1$ to $C_8$ alkyl esters, the phenyl, benzyl, and menthyl esters, but others will be apparent to those skilled in the art.

Suitably the antibacterial component comprises 10–40% by weight of benzyl-p-hydroxybenzoate, 15–50% by weight of menthyl-o-hydroxybenzoate (menthyl salicylate) and 30–70% by weight of phenyl-o-hydroxybenzoate (phenyl salicylate).

Preferably the antibacterial component consists of 10 to 40% by weight of benzyl-p-hydroxybenzoate, 15–50% by weight of menthyl salicylate, 1 to 10% by weight of o-phenylphenol and 1 to 10% by weight of phenoxyethanol.

Preferably the vitamin component comprises 0.02 to 2.0% of aescin, 0.05 to 2.0% of panthenol, 0.1 to 1.0% of nicotinamide and 0.01 to 0.5% of vitamin E, those percentages being by weight of the total oral hygiene composition.

The vitamin component may comprise small amounts of other vitamins such as vitamin C, vitamin K, and B group vitamins.

The surfactant component preferably comprises one or more anionic surfactants, (e.g. fatty alkylsulphates and fatty alkylether-sulphates with a chain length of 12 to 18 carbon atoms and up to 4 ethyleneoxide units; synthetic alkylsulphates and alkylethersulphates with a chain length of 12 to 15 carbon atoms and up to 4 ethyleneoxide units) the cation being for example sodium, potassium, magnesium, ammonium or triethanolammonium. Cationic surfactants, although not preferred, could be used, e.g. quaternary surfactants.

The preferred form of presentation for the oral hygiene compositions of this invention is a mouthwash. In this case, the balance of the composition apart from the antibacterial, vitamin and surfactant components may be a liquid vehicle, containing flavouring agents, sweeteners, dyestuffs, thickeners, antioxidants and the like. The liquid vehicle is preferably one which will dissolve the other ingredients of the composition and suitable vehicles include aqueous ethanol, aqueous isopropanol, aqueous n-propanol, aqueous sorbitol, aqueous glycerol, aqueous 1,2-propyleneglycol and aqueous 1,4-butanediol. Conventional flavouring agents include peppermint oil, spearmint oil, wintergreen oil, aniseed oil, clove oil, eucalyptus oil, cinnamon oil, geranium oil, coriander oil, menthol, anisol and anethol. Conventional sweeteners include sodium saccharine and sodium cyclamate.

In addition to the three essential components, the liquid vehicle and conventional flavouring agents etc., a composition in accordance with this invention may include compatible anticariogenic fluoride components such as alkali or alkaline earth metal (e.g. sodium or stannous) and ammonium fluorides and fluorophosphates (especially sodium monofluorophosphate) in conventional pharmaceutically acceptable amounts.

The three specified components of the composition of this invention are present in amounts of from 0.1 to 5.0%. It is to be understood that in general, a composition which is to be ready to use directly (e.g. a toothpaste or chewing gum) will contain amounts of these components towards the lower end of this range, whereas a composition which is to be diluted (e.g. a mouthwash concentrate) will contain amounts of the components towards the upper end of this range.

Oral hygiene compositions according to this invention may also be presented as toothpastes and chewing gums by compounding the three essential components (antibacterial, vitamin and surfactant components) together with conventional toothpaste ingredients or gum ingredients.

The following Examples illustrate embodiments of this invention:

EXAMPLE I

A mouthwash was prepared by simple mixing with stirring according to the following compositions:

| | | |
|---|---|---|
| n-propanol | 65 | percent (by weight) |
| 1,2-propyleneglycol | 10 | " |
| phenylsalicylate | 0.3 | " |
| menthylsalicylate | 0.2 | " |
| benzyl-p-hydroxybenzoate | 0.2 | " |
| o-phenylphenol | 0.01 | " |
| phenoxyethanol | 0.02 | " |
| triethanolaminelarylsulphate | 0.50 | " |
| d-panthenol | 0.25 | " |

-continued

| | | |
|---|---|---|
| nicotinamide | 0.5 | " |
| aescin | 0.15 | " |
| vitamin-E-acetate | 0.1 | " |
| sodium-saccharinate | 0.3 | " |
| flavour+) | 4.0 | " |
| distilled water | 18.47 | " |
| | 100.00 | percent |
| +) composition of the flavour: | | |
| peppermint oil | 75 | percent (by weight) |
| menthol | 10 | " |
| eucalyptol | 3 | " |
| anethol | 8 | " |
| clove oil | 4 | " |
| | 100 | " |

There was obtained a clear, slightly yellow solution which on dilution with water (distilled) especially in the range of 0.5 to 5 percent by weight showed a very pleasant and refreshing taste and odour.

EXAMPLE II

A toothpaste in accordance with the present invention was made up in accordance with the following formula:

| | | |
|---|---|---|
| glycerin | 25 | percent (by weight) |
| sodium carboxymethylcellulose | 1 | " |
| sodium monofluorophosphate | 0.80 | " |
| aescin | 0.10 | " |
| panthenol | 0.50 | " |
| nicotinamide | 0.80 | " |
| vitamin E acetate | 0.10 | " |
| dicalcium phosphate | 45 | " |
| sodium lauryl sulphate | 2 | " |
| benzyl p-hydroxybenzoate | 0.40 | " |
| menthyl salicylate | 0.40 | " } 1% |
| o-phenylphenol | 0.10 | " |
| phenoxyethanol | 0.10 | " |
| flavouring | q.s. | |
| water | to 100% | |

BIOLOGICAL RESULTS

For comparison purposes, the following mouthwash compositions were made up as follows:

I. In a mixture consisting of 65 parts by weight of n-propanol and 10 parts by weight of 1,2-propyleneglycol there was dissolved 4 parts by weight of the flavour indicated in Example 1, 0.3 parts by weight of sodium-saccharinate and 20.7 parts by weight of distilled water. A clear, slightly yellow solution was obtained which on dilution with distilled water especially in the range of 0.5 to 5 percent by weight showed a very pleasant and refreshing taste and odour.

II. A mouthwash was prepared according to the following formula:

| | | |
|---|---|---|
| n-propanol | 65 | percent (by weight) |
| 1,2-propyleneglycol | 10 | " |
| phenylsalicylate | 0.3 | " |
| menthylsalicylate | 0.2 | " |
| benzyl-p-hydroxybenzoate | 0.2 | " |
| o-phenylphenol | 0.01 | " |
| phenoxyethanol | 0.02 | " |
| triethanolaminelaurylsulphate | 0.5 | " |
| sodium-saccharinate | 0.3 | " |
| flavour (as indicated in Example 1) | 4.0 | " |
| distilled water | 19.47 | " |
| | 100.00 | percent |

The composition of this preparation is identical to that indicated in Example 1 with the exception of the vitamin component which has been omitted.

III. A mouthwash was prepared according to the following formula:

| | | |
|---|---|---|
| n-propanol | 65 | percent (by weight) |
| 1,2-propyleneglycol | 10 | " |
| triethanolaminelaurylsulphate | 0.5 | " |
| sodium-saccharinate | 0.3 | " |
| d-panthenol | 0.25 | " |
| nicotinic acid amide | 0.50 | " |
| aescin | 0.15 | " |
| vitamin-E-acetate | 0.10 | " |
| flavour (as indicated in Example 1) | 4.00 | " |
| distilled water | 19.20 | " |
| | 100.00 | percent |

The composition of this preparation is identical to that indicated in Example I with the exception of the antibacterial component which has been omitted.

In addition two mouthwash compositions of the prior art were made up as follows:

IV. A mouthwash was prepared according to the instructions given in British Pat. No. 1308483, Example 4:

| | | |
|---|---|---|
| sodiumfluorophosphate | 1.30 | percent (by weight) |
| rutin (as rutinsodiumsulphate) | 0.20 | " |
| disodiumglycerophosphate | 2.50 | " |
| potassiumdihydrogenphosphate | 1.20 | " |
| disodiumhydrogenphosphate | 1.30 | " |
| flavours and sweeteners | 1.30 | " |
| cetylpyridiniumchloride | 0.20 | " |
| glycerin (86%) | 8.00 | percent |
| ethanol (90%) | 40.00 | " |
| water | 44.00 | " |
| | 100.00 | percent |

A slightly yellow solution resulted which on dilution with distilled water especially in the range of 0.5 to 5 per cent by weight showed a rather bitter and unpleasant taste.

V. Mouthwash preparation containing chlorhexidinegluconate as known in the art.

The following mouthwash composition was prepared by mixing with stirring:

| | | |
|---|---|---|
| chlorhexidinegluconate | 0.2 | percent (by weight) |
| trichlorobutanol | 0.1 | " |
| methyl-p-hydroxybenzoate | 0.2 | " |
| propyl-p-hydroxybenzoate | 0.2 | " |
| chloroform | 0.5 | " |
| sodium-dioctyl-sulfo-succinate | 0.1 | " |
| peppermint oil DAB 7 | 1.5 | " |
| menthol | 0.15 | " |

| | |
|---|---|
| ethanol (94%) | 45.00 " |
| glycerol (86%) | 35.00 " |
| water (distilled) | 17.05 " |
| | 100.00 percent |

There was obtained a clear, slightly yellow solution which on dilution with distilled water especially in the range of 0.5–5 percent by weight was characterised by an unpleasant taste and odour.

Comparison Tests

Aqueous preparations containing 5 percent by weight of each of the mouthwashes I – V and that of Example I tested under the conditions of the broth dilution test, as proposed by the German Society for Hygiene and Microbiology. ("Richtlinien fuer die Pruefung chemischer Desinfektionsmittel", Ueberarbeitete und ergaenzte Auflage Gustav Fischer-Verlag, Stuttgart, 1969). The time (in min) which was necessry for killing of the different bacteria strains (which are also present in the cavity of the mouth frequently) was as follows:

| Organism | Test Composition Example | | | | | |
|---|---|---|---|---|---|---|
| | IV | V | 1 | I | II | III |
| streptococcus haemolyticus | 10 | 30 | 1 | 30 | 10 | 30 |
| Proteus vulgaris | 10 | >30 | 1 | 10 | 5 | 10 |
| Candida albicans | 20 | >30 | 5 | >30 | 20 | >30 |

There is no doubt from the figures that the preparation relating to the invention (Example I) is superior to the comparison preparations especially to the Chlorhexidine preparation V.

In a double blind study involving 95 patients (male and female), the mouthwash of Example I was superior (p < 0.005% by both the nonparametric Mann-Whitney U-Test-Sidney Siegel. "Nonparametric Statistics for Behavioural Sciences", MacGraw Hill 1956 — and the parametric t-test) to the placebo (comparison preparation I) in the treatment of periodontal diseases such as gingivitis, periodontitis and papillitis. The patients were instructed to use one of the two test mouthwashes (coded but not identified) for three weeks, three times daily in concentration of 2–5% by weight (dilutions to be made with warm tap water) in addition to normal tooth brushing, and return for inspection after 10 and 21 days.

Visual inspections were made according to a modified Silness and Loe gingival index system (see T. Silness and H. Loe, 1963, Acta odont. Scand. 21: 533–551) at the beginning, middle and end of the study.

We claim:

1. An oral hygiene composition for the prophylaxis and treatment of inflammatory diseases of the periodontium comprising an antibacterial component in an amount of from 0.1 to 5.0%, a vitamin component in an amount of from 0.1 to 5.0% and a surfactant component in an amount of from 0.1 to 5.0%, these percentages being by weight of the total composition, the weight ratio of antibacterial component to surfactant being from 1:5 to 5:1, the antibacterial comprising one or more pharmaceutically acceptable esters of p-hydroxybenzoic acid or one or more pharmaceutically acceptable esters of o-hydroxybenzoic acid or both, and the vitamin component comprising one or more of the following aescin, rutin, panthenol, nicotinamide and vitamin E, no ingredient of the total composition being present in more than a pharmaceutically acceptable amount.

2. An oral hygiene composition as claimed in claim 1 wherein the antibacterial component comprises 10 to 40% by weight of one or more pharmaceutically acceptable esters of p-hydroxybenzoic acid and 30 to 90% by weight of one or more pharmaceutically acceptable esters of o-hydroxybenzoic acid.

3. An oral hygiene composition as claimed in claim 1 wherein the antibacterial component comprises 10–40% by weight of benzyl-p-hydroxybenzoate, 15–50% by weight of menthyl-o-hydroxybenzoate and 30–70% by weight of phenyl-o-hydroxybenzoate.

4. An oral hygiene composition as claimed in claim 1 wherein the antibacterial component consists of 10 to 40% by weight of benzyl-p-hydroxybenzoate, 15–50% by weight of menthyl salicylate, 1 to 10% by weight of o-phenylphenol and 1 to 10% by weight of phenoxyethanol.

5. An oral hygiene composition as claimed in claim 1 wherein the vitamin component comprises 0.02 to 2.0% of aescin, 0.05 to 2.0% of panthenol, 0.1 to 1.0% of nicotinamide and 0.01 to 0.5% of vitamin E, those percentages being by weight of the total oral hygiene composition.

6. An oral hygiene composition as claimed in claim 1 wherein the surfactant component comprises one or more anionic surfactants.

7. An oral hygiene composition as claimed in claim 6 wherein the anionic surfactant is a member of the group consisting of fatty alkylsulphates and fatty alkylethersulphates with a chain length of 12 to 18 carbon atoms and up to 4 ethyleneoxide units; synthetic alkylsulphates and alkylethersulphates with a chain length of 12 to 15 carbon atoms and up to 4 ethylenoxide units, the cation being sodium, potassium, magnesium, ammonium or triethanolammonium.

8. An oral hygiene composition as claimed in claim 1 which is in the form of a mouthwash.

9. An oral hygiene composition as claimed in claim 1 which is in the form of a toothpaste or chewing gum.

10. An oral hygiene composition as claimed in claim 1 which includes an alkali or alkaline earth metal or ammonium fluoride or fluorophosphate.

11. An oral hygiene composition as claimed in claim 10 which includes sodium or stannous fluoride or sodium monofluorophosphate.

* * * * *